United States Patent
Ishikawa et al.

(10) Patent No.: US 8,933,118 B2
(45) Date of Patent: Jan. 13, 2015

(54) ANTI-BRAIN-TUMOR DRUG

(75) Inventors: Yoshihiro Ishikawa, Tokyo (JP); Haruki Eguchi, Kawasaki (JP)

(73) Assignee: IHI Corporation, Tokyo (JP)

( * ) Notice: Subject to any disclaimer, the term of this patent is extended or adjusted under 35 U.S.C. 154(b) by 0 days.

(21) Appl. No.: 13/643,612

(22) PCT Filed: Apr. 11, 2011

(86) PCT No.: PCT/JP2011/002118
§ 371 (c)(1),
(2), (4) Date: Feb. 6, 2013

(87) PCT Pub. No.: WO2011/135784
PCT Pub. Date: Nov. 3, 2011

(65) Prior Publication Data
US 2013/0131367 A1     May 23, 2013

(30) Foreign Application Priority Data

Apr. 28, 2010 (JP) .................................. 2010-102897

(51) Int. Cl.
| | | |
|---|---|---|
| C07F 15/02 | (2006.01) | |
| A61K 31/28 | (2006.01) | |
| C07C 251/24 | (2006.01) | |
| C07F 13/00 | (2006.01) | |
| C07F 15/00 | (2006.01) | |

(52) U.S. Cl.
CPC ............. C07F 15/025 (2013.01); C07C 251/24 (2013.01); C07F 13/005 (2013.01); C07F 15/0013 (2013.01)
USPC .......................................... 514/492; 556/32

(58) Field of Classification Search
USPC ............................................ 556/32; 514/492
See application file for complete search history.

(56) References Cited

U.S. PATENT DOCUMENTS

| | | | | |
|---|---|---|---|---|
| 5,696,109 | A * | 12/1997 | Malfroy-Camine et al. | . 514/185 |
| 6,046,188 | A | 4/2000 | Malfroy-Camine et al. | |
| 8,198,322 | B2 * | 6/2012 | Mandal et al. ................ | 514/492 |
| 2009/0169484 | A1 * | 7/2009 | Eguchi et al. ................ | 424/9.36 |
| 2009/0326061 | A1 | 12/2009 | Mandal et al. | |
| 2012/0029167 | A1 | 2/2012 | Ishikawa et al. | |

FOREIGN PATENT DOCUMENTS

| | | |
|---|---|---|
| EP | 2357166 A1 | 8/2011 |
| JP | H11507646 | 7/1999 |
| JP | 2009173631 A | 8/2009 |
| JP | 2009196913 A | 9/2009 |
| WO | 9413300 A1 | 6/1994 |
| WO | 0180849 A1 | 11/2001 |
| WO | 2010058280 A1 | 5/2010 |
| WO | 2010120875 A2 | 10/2010 |

OTHER PUBLICATIONS

Database CA, Chemical Abstracts Service, Columbus, Ohio, US; Malfroy-Camine, Bernard et al., "Synthetic catalytic free radical scavengers useful as antioxidants for prevention and therapy of disease", retrieved from STN Database accession No. 1997:130022.
Bechtel, Wikbe et al., "Modulation of Intercellular ROS Signaling of Human Tumor Cells", Anticancer Research 29; 4559-4570 (2009).
Woldemariam et al., "Iron(III)-salen damages DNA and induces apoptosis in human cell via mitochondrial pathway", Journal of Inorganic Biochemistry 102 (2008) pp. 740-747.
European Search Report, European Patent Appln. No. 11774575.2, Sep. 2, 2013, 13 pp.
Japanese Office Action, Japanese Patent Appln. No. 2012-512639, Oct. 29, 2013, 4 pp.

* cited by examiner

*Primary Examiner* — Porfirio Nazario Gonzalez
(74) *Attorney, Agent, or Firm* — Volpe and Koenig, P.C.

(57) ABSTRACT

A drug containing a metal-salen complex compound which is effective for a brain tumor is provided. The present invention is an anti-brain-tumor drug containing a metal-salen complex compound represented by the following Chemical Formula (I). In the formula, M represents a metal atom which is Fe, Cr, Mn, Co, Ni, Mo, Ru, Rh, Pd, W, Re, Os, Ir, Pt, Nd, Sm, Eu, or Gd, and X represents a halogen atom.

Chemical Formula (I)

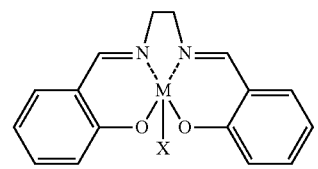

6 Claims, 3 Drawing Sheets

TAKING IMAGE FROM THIS END
TO THE OTHER END ON THE OTHER SIDE

ANTI-BRAIN-TUMOR DRUG

TECHNICAL FIELD

The present invention relates to anti-brain-tumor drugs.

BACKGROUND ART

After a drug is administered to a living body, it reaches an affected site and exerts its pharmacological effects at that affected site, thereby exerting its therapeutic effects. On the other hand, even if the drug reaches tissue other than the affected site (that is, normal tissue), it will not be therapeutic, but also cause adverse reactions.

Therefore, how to guide the drug to the affected site is important in terms of therapeutic strategies. A technique to guide the drug to the affected site is called drug delivery, which has been actively studied and developed recently. This drug delivery has at least two advantages.

One advantage is that a sufficiently high drug concentration can be obtained at the affected site tissue. Pharmacological effects will not be seen unless the drug concentration at the affected site is a constant value or more. This is because the therapeutic effects cannot be expected if the concentration is low. The second advantage is that the drug is guided to only the affected site tissue and will not be guided to the normal tissue unnecessarily. As a result, adverse reactions can be inhibited.

Such drug delivery is most effective for a cancer treatment by anti-tumor agents. Most anti-tumor agents inhibit the cell growth of cancer cells which divide actively, so that the anti-tumor agents will also inhibit the cell growth of even the normal tissue in which cells divide actively, such as bone marrow, hair roots, or alimentary canal mucosa.

Therefore, cancer patients to whom the anti-tumor agents are administered suffer adverse reactions such as anemia, hair loss, and vomiting. Since such adverse reactions impose heavy burdens on the patients, the dosage needs to be limited, thereby causing a problem of incapability to sufficiently obtain the pharmacological effects of the anti-tumor agents.

So, it is expected to inhibit the adverse reactions and perform the cancer treatment effectively by guiding the anti-tumor agents to the cancer cells by means of the drug delivery and making the anti-tumor agents exert the pharmacological effects intensively on the cancer cells.

The applicant of the present application suggested an iron-salen complex as an example of such anti-tumor agents. Since this iron-salen complex is magnetic itself, it can be guided to the target affected site tissue by means of an external magnetic field without using a magnetic carrier. (See, for example, Patent Literature 1).

Citation List

Patent Literature

[Patent Literature 1] Japanese Patent Application Laid-Open (Kokai) Publication No. 2009-173631

SUMMARY OF INVENTION

After thorough examination, the inventors of the present invention have found that the above-described iron-salen complex cannot pass a blood-brain barrier, thereby causing a problem of insufficient applicability to a brain tumor.

Therefore, it is an object of the present invention to provide a metal-salen complex effective for the brain tumor.

After thorough examination, the inventors of the present invention have found that a metal-salen complex compound with a functional group constituting anions bonded to a trivalent metal atom is bonded has the property to be capable of passing the blood-brain barrier while maintaining its magnetism; and the metal-salen complex compound can be guided selectively from blood vessels to the brain tumor by applying the external magnetic field to the affected site where the brain tumor is located. Examples of the functional group constituting this type of anions include halogen atoms, a hydroxyl group, an amide group, and a carboxyl group and a preferred example of the functional group is halogen atoms, among which particularly a chlorine atom is desirable.

Specifically speaking, for example, an anti-brain-tumor drug is characterized in that it contains a metal-salen complex compound represented by the following Chemical Formula (I), a pharmacologically-allowable derivative, and/or a pharmacologically-allowable salt.

Chemical Formula (I)

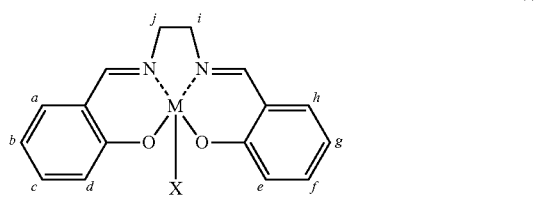

In the formula (I), M represents Fe (iron), Cr (chromium), Mn (manganese), Co (cobalt), Ni (nickel), Mo (molybdenum), Ru (rubidium), Rh (rhodium), Pd (palladium), W (tungsten), Re (rhenium), Os (osmium), Ir (iridium), Pt (platinum), Nd (niobium), Sm (samarium), Eu (europium), or Gd (gadolinium); at least one of a to j is a substituent that maintains the effects of the metal-salen complex, and the rest of them is hydrogen; and X represents a halogen atom. Such a substituent is described in, for example, WO2010/058280. A preferred metal-salen complex compound is structured so that M is an iron atom, X is a chlorine atom, and all of a to j are hydrogen atoms.

Advantageous Effects of Invention

A metal-salen complex compound having the therapeutic effects for the brain tumor can be provided according to the present invention as described above.

DESCRIPTION OF EMBODIMENTS

Figure 1:
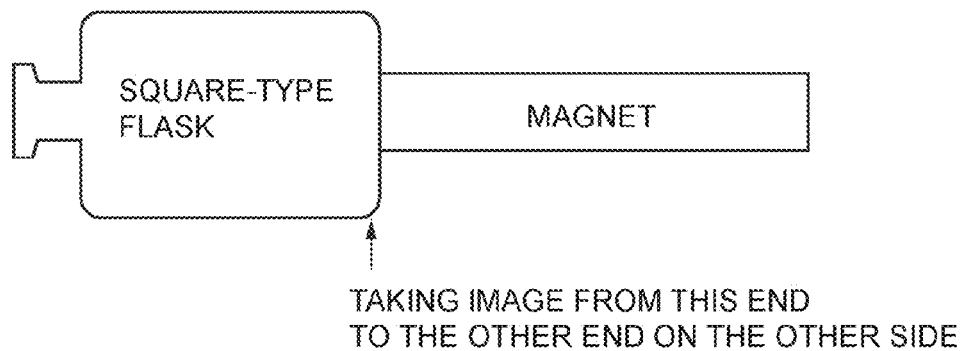
FIG. 1 is a side view (diagrammatic illustration) of a state where a magnet rod is made to be in contact with a square-type flask containing a culture medium of rat L6 cells.

<Synthesis of Iron-Salen Complex (Chemical Formula I)>

Step 1:

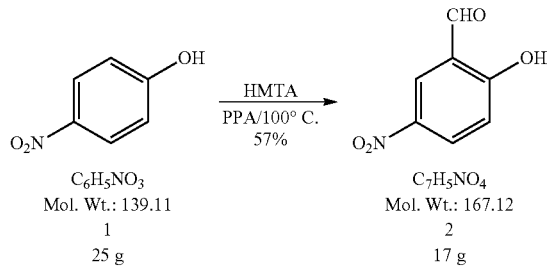

A mixture of 4-nitrophenol (Compound 1) (25 g, 0.18 mol), hexamethylene tetramine (25g, 0.18 mol), and polyphosphoric acid (200 ml) were stirred for one hour at the temperature of 100 degrees Celsius. Then, that mixture was introduced to 500 ml of ethyl acetate and 1 L (liter) of water and stirred until it completely dissolves. Furthermore, when 400 ml of ethyl acetate was added to that solution, the solution separated into two phases. Subsequently, the aqueous phase was removed from the solution which separated into the two phases; and the remaining compound was washed twice with a basic solvent and dried over anhydrous $MgSO_4$ (magnesium sulfate). As a result, 17 g of Compound 2 (57% yield) was synthesized.

Step 2:

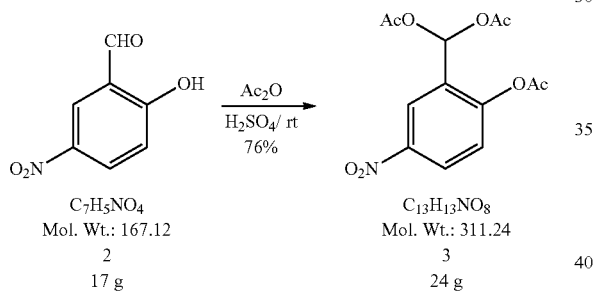

Compound 2 (17g, 0.10 mol), acetic anhydride (200 ml) and $H_2SO_4$ (minimal) were stirred for one hour at room temperature. The resulting solution was mixed for 0.5 hour in iced water (2 L) to bring about hydrolysis. The resulting solution was filtered and dried in air, thereby obtaining white powder. The powder was recrystallized, using a solvent containing ethyl acetate. As a result, 24 g of Compound 3 (76% yield) was obtained in the form of white crystals.

Step 3:

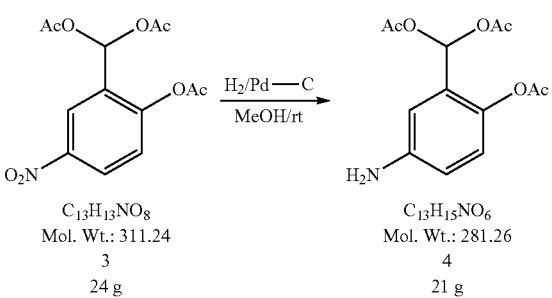

A mixture of carbon (2.4 g) supporting 10% palladium with Compound 3 (24 g, 77 mol) and methanol (500 ml) was reduced over night in a 1.5 atm hydrogen reducing atmosphere. After the reduction was completed, the product was filtered, thereby allowing 21 g of Compound 4 in the form of brown oil to be synthesized.

Steps 4 and 5:

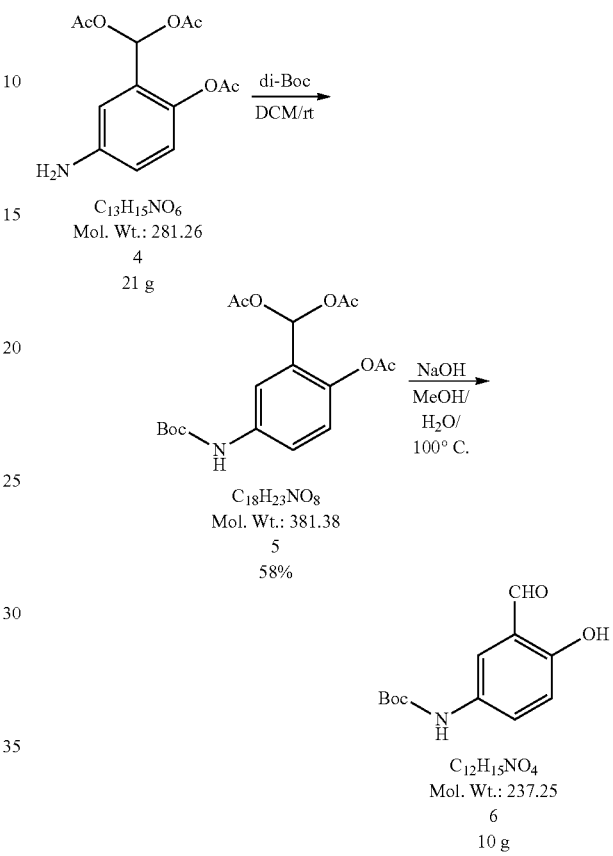

Compound 4 (21 g, 75 mmol) and di(tert-butyl)dicarbonate (18 g, 82 mmol) were stirred over night in anhydrous dichloromethane (DCM) (200 ml) in a nitrogen atmosphere. The resulting solution (Compound 5) was allowed to evaporate in a vacuum and then dissolved in methanol (100 ml). Sodium hydroxide (15 g, 374 mmol) and water (50 ml) were then added and the solution was brought to reflux for 5 hours. The solution was then cooled, filtered, washed with water, and allowed to dry in a vacuum, thereby obtaining a brown compound. The resulting compound was processed twice by flash chromatography using silica gel, thereby obtaining 10 g of Compound 6 (58% yield).

Step 6:

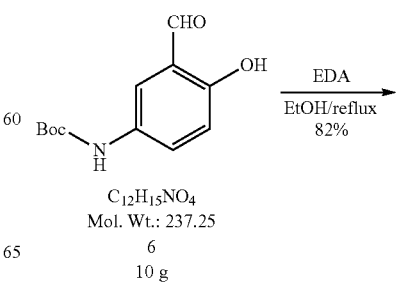

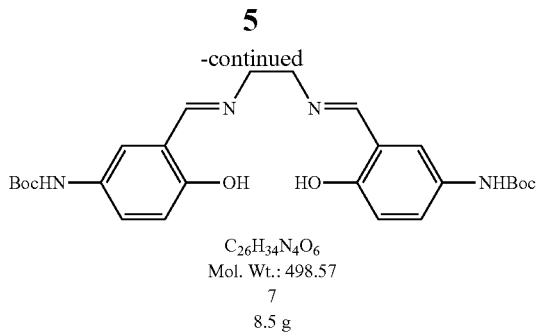

C₂₆H₃₄N₄O₆
Mol. Wt.: 498.57
7
8.5 g

Compound 6 (10 g, 42 mmol) was introduced into 400 ml of anhydrous ethanol, the mixture was brought to reflux while heated, and several drops of ethylene diamine (1.3 g, 21 mmol) were added into 20 ml of anhydrous ethanol while stirred for 0.5 hour. The mixture was introduced into a container of ice, where it was cooled and mixed for 15 minutes. It was then washed with 200 ml of ethanol, filtered, and dried in a vacuum, thereby obtaining 8.5 g (82% yield) of Compound 7.

Step 7:

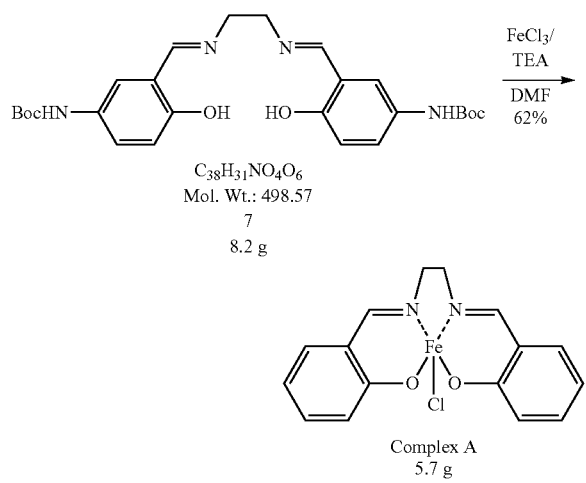

Compound 7 (8.2 g, 16 mmol) and triethylamine (22 ml, 160 mmol) were introduced into N,N-dimethylformamide (abbreviated as DMF) (50 ml), and a solution of $FeCl_3 \cdot 4H_2O$ (iron (III) chloride solution) (2.7 g, 16 mmol) added to 10 ml of methanol was mixed in a nitrogen atmosphere. The ingredients were mixed for 30 minutes in a nitrogen atmosphere at the temperature of 40 degrees Celsius, thereby obtaining a brown compound.

Subsequently, this compound was then dried in a vacuum. The resulting compound was diluted with 400 ml of dichloromethane, washed twice with a basic solution, dried in $Na_2SO_4$ (sodium sulfate), and dried in a vacuum, thereby obtaining an iron-salen complex. The resulting compound was recrystallized in a solution of diethyl ether and paraffin, and assay by high performance liquid chromatography revealed 5.7 g (62% yield) of the iron-salen complex with a purity of 95% or higher.

<Pharmacological Effects of Iron-Salen Complex (Chemical Formula (I))>

Powder of the iron-salen complex compound represented by Chemical Formula (I) was applied, in an amount (50 mg) to the degree allowing its magnetic attraction to be visibly observed, to a culture medium when the rat L6 cells were in a 30% confluent state; and the state of the culture medium was photographed after 48 hours.

FIG. 1 shows a state in which a magnet rod is in contact with a square-type flask containing the rat L6 cell culture medium. After 48 hours, an image of the bottom of the square-type flask was photographed from one end to the other end and the number of cells was calculated. This result is shown in FIG. 2.

Figure 2:
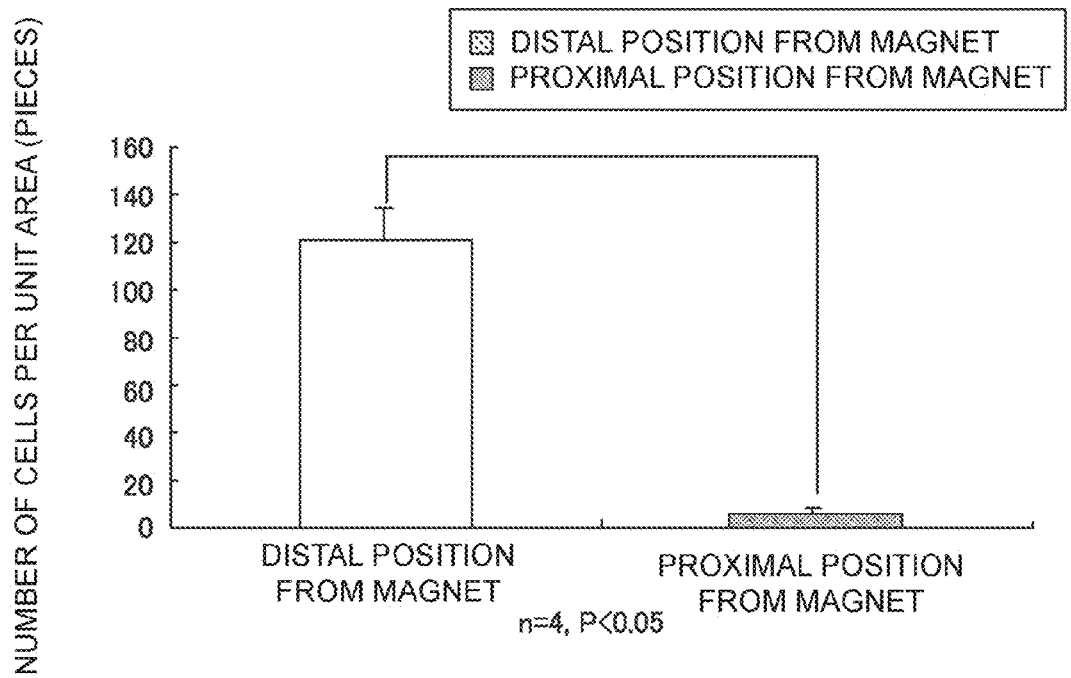
FIG. 2 is a graph showing the calculation results of the number of cells by taking an image from one end to the other end of the bottom of the square-type flask after 48 hours.

Referring to FIG. 2, a proximal position from the magnet indicates within a project area of the magnet end face on the bottom of the square-type flask and a distal position from the magnet indicates an area on the opposite side of the magnet end face on the bottom of the square-type flask. FIG. 2 shows that a concentration of the iron complex increases as the iron complex is attracted at the proximal position from the magnet. So, it can be seen that the number of cells becomes extremely lower than that at the distal position due to a DNA-growth inhibition action of the iron complex.

Figure 3:
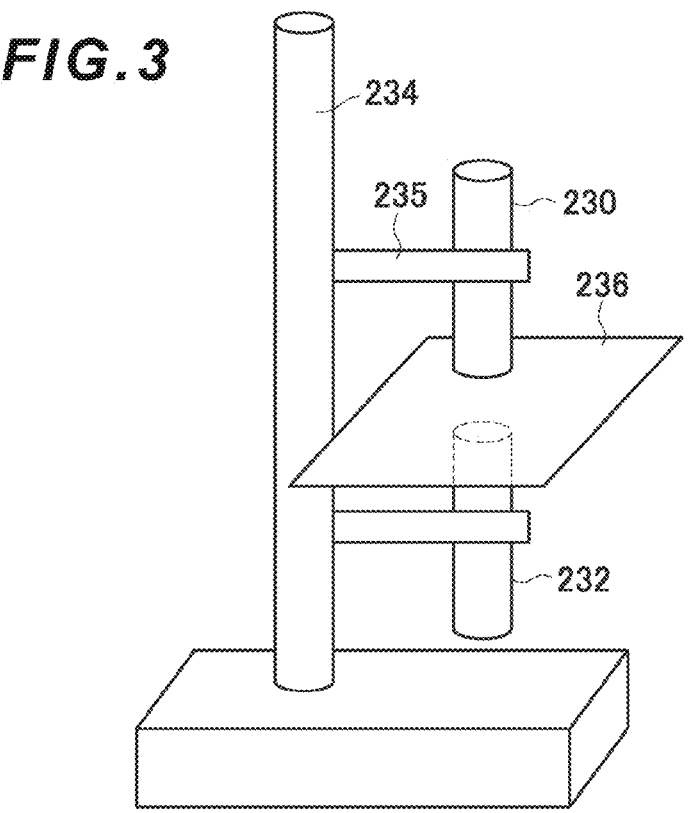
FIG. 3 is a perspective view showing an example of a magnetic delivery device.

Next, an embodiment in which a magnetic field is applied from a delivery device to an individual and the iron-salen complex is guided to the individual's brain will be explained. With this delivery device, as illustrated in FIG. 3, a pair of magnets 230 and 232 facing each other in the direction of gravity are supported by a stand 234 and a clamp 235, and a metal plate 236 is located between the magnets 230 and 232. A magnetic field of uniform strength can be created locally by placing the metal plate 236, especially an iron plate, between the pair of magnets 230 and 232.

Incidentally, an electrical magnet can be used instead of the magnet to modify the magnetic force generated in this delivery device. The magnetism-generating means can be moved to a target position of the individual on a table to allow the pair of magnetism-generating means to move in X, Y, and Z directions.

The drug can be concentrated on specific tissue by placing the individual in the region of the magnetic field. After intravenously injecting the aforementioned metal complex (drug concentration: 5 mg/ml (15 mmol)) to veins of a tail of a mouse weighing about 30 g, the mouse's head was placed between the magnets. Another individual to which the iron-salen complex was applied under the same conditions without applying the magnetic field was prepared as a comparison target. Incidentally, the individual to which the magnetic field is applied will be referred to as the specimen and the individual to which the magnetic field is not applied will be referred to as the object.

The magnets used were Product No. N50 (neodymium permanent magnets) by Shin-Etsu Kagaku Kogyo, with a residual flux density of 1.39 to 1.44 tesla (T). The mice's brains were removed after the experiments and staining (Prussian blue; ferric hexaacyanoferrate and hydrochloric acid, Sigma) was applied to them. As a result of comparison between the specimen and the object, the brain tissue of the specimen was stained blue.

23% of the brain tumor, which is a brain cancer, is a cancer called meningioma that is produced in the meninges (area closest to the skull in the skull). The compound of Chemical Formula (I) can be guided efficiently from the veins to the meninges. Since the magnetic field is applied externally, the compound of Chemical Formula (I) is effective for particularly the meningioma produced at the meninges immediately below the skull.

<Magnetism of Iron-Salen Complex>

Figure 4:
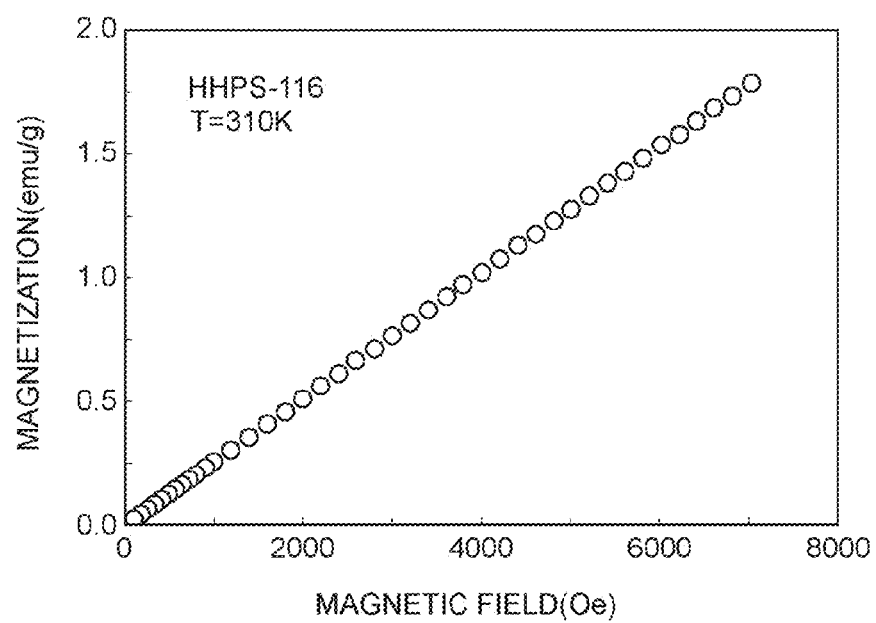
FIG. 4 is a graph showing the magnetic property of the metal-salen complex compound.

When a magnetic field-magnetization curve of the iron-salen complex (Chemical Formula (I)) was measured at the temperature of 37 degrees Celsius (310K) by using MPMS7 by Quantum Design, Inc., paramagnetism was observed as shown in FIG. 4. As a result, the metal-salen complex can be guided selectively to a tumor-produced site in the head by exogenously applying 8000 Oe (0.8 T) magnetic field intensity to the tumor-produced site of the head. The magnetic field intensity within the range from 0.5 T to 0.8 T is desirable for use in guiding the drug to the head.

<Crystal Analysis>

A single crystal analysis of the iron-salen complex (Chemical Formula (I)) was performed by using Super Photon Ring -8 (Spring-8). The details of X-ray structure analysis are as follows.

Used Facility: Spring-8
Provisional Irradiation Conditions: five crystals were selected and provisional irradiation was performed under the following conditions.
Detector: imaging plate
Camera length: 190 mm
Wavelength: 0.0710690 nm
Vibrational angle: 2.0 degrees
Exposure time: 30 seconds
Measuring range: 0 to 20 degrees
Measurement temperature: −173 degrees Celsius As a result of the provisional irradiation, it was judged with respect to one of the five crystals that its diffraction pattern was comparatively clear and the structure analysis can be performed. So, that crystal was decided to be a target of actual irradiation.

Actual Irradiation Conditions: the actual irradiation was performed under the following conditions.
Detector: imaging plate
Camera length: 190 mm
Wavelength: 0.0710690 nm
Vibrational angle: 1.0 degrees
Exposure time: 90 seconds
Measuring range: −90 to +90 degrees
Measurement temperature: −173 degrees Celsius As a result of processing of 180 pieces of image data obtained by the actual irradiation, crystal parameters were decided as follows.
Crystal system: monoclinic
Lattice constants:
a=14.34(6) Å
b=6.907(16) Å
c=14.79(4) Å
β=96.73(4) degrees
V=1455(8) Å$^3$
Space group: P21/n (#14)
Z value: 4
Measurement scale: −90° to 90°

Figure 5:
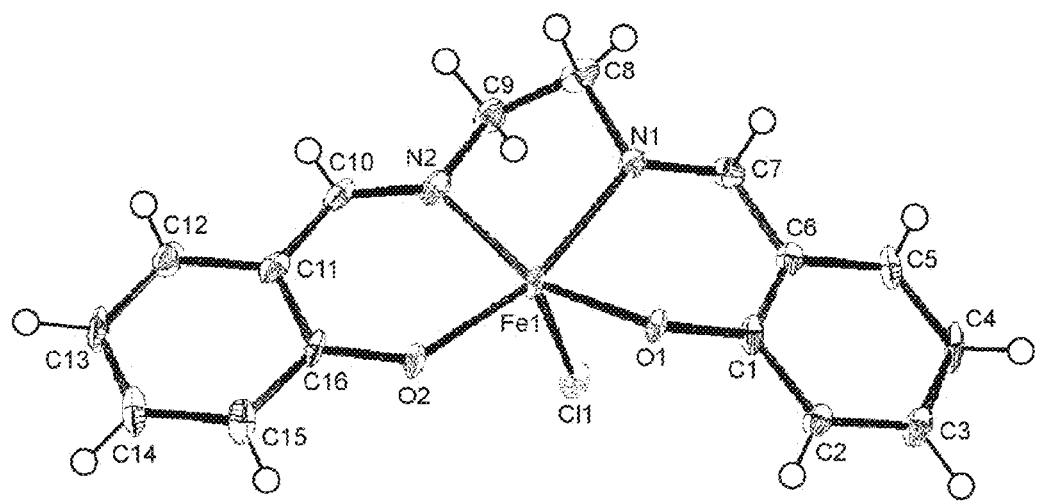
FIG. 5 is a molecular model showing a first structure of the iron-salen complex compound.

As a result of analysis by a direct method, a predicted complex structure (FIG. 5) was confirmed; however, the existence of an unknown peak was observed near the Fe atom. It was thought based on the distance from the Fe atom and the peak height that it must be an atom other than C, H, Fe, N, or O. As a result of EPMA analysis performed in order to identify the unknown peak, the existence of chlorine was found. Furthermore, when the result of EI/MS measurement was checked, chlorine adducts were detected. As a result, the unknown peak was judged as the chlorine atom.

Figure 6:
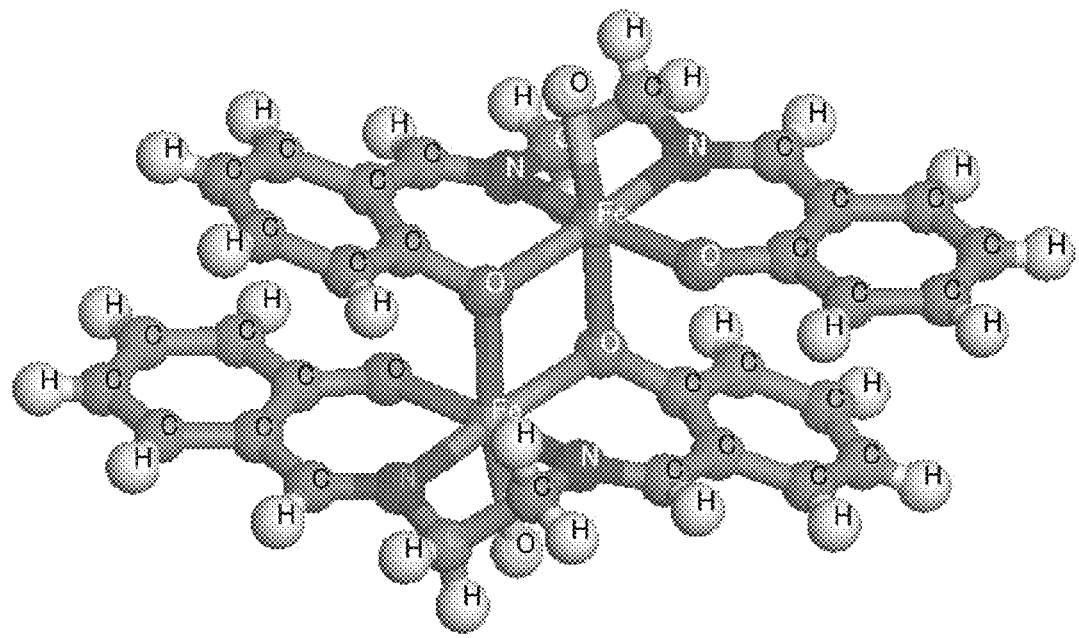
FIG. 6 is a molecular model showing a second structure of the iron-salen complex compound.

A refined final molecular structure is shown in FIG. 6. Since each parameter did not particularly show any abnormal value in the result of a last cycle of a method of least squares, it was determined that the last structure shows an accurate composition. Incidentally, it was found that two molecules in the crystal form an aggregate (dinuclear complex) via the Fe and O atoms.

<Water Solubility of Iron Complex Compound (Chemical Formula I)>

Free energy of water solubility of the chemical formula I was calculated by using a first principle calculation. The entire first principle calculation is based on density functional formalism. An all-electron method of considering all electrons is used with respect to interactions between electrons and ions.

Regarding a wave function, a double-numeric basis function (Double Numerical basis-set including Polarization function, DNP) to which a polarization function is added for a spin-polarized, linear-combination atomic orbitals (Liner Combination of Atomic Orbitals, LCAO) was used and cutoff of the above-mentioned basis function was set to 0.4 nm in order to increase the calculation speed without impairing the calculation accuracy.

Exchange correlation term by Becke, Lee, Yang, Parr were used and software used was DMol3 by Accelrys K.K. The energy of water solubility was calculated by a method by Andreas Klamt, COSMO-RS: From Quantum Chemistry to Fluid Phase Thermodynamics and Drug Design, 2005, Elsevier. As a result, the free energy of water solubility of the iron-salen complex of the following Chemical Formula (II) was −20.13 kcal/mol. On the other hand, the free energy of water solubility of the iron chloride-salen complex of Chemical Formula (I) was −31.95 kcal/mol, so that the chlorine-added iron-salen complex of Chemical Formula (I) has higher water solubility.

Chemical Formula (II)

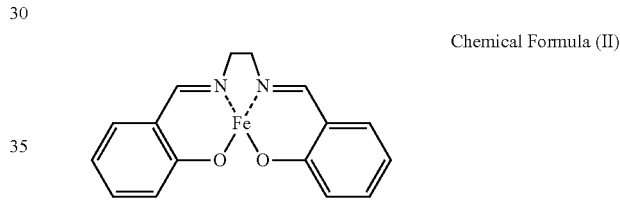

The invention claimed is:

1. An anti-brain-tumor drug containing, as its main component, a metal-salen complex compound with a functional group constituting anions bonded to a trivalent metal atom to pass through a blood-brain barrier when applied systematically,
wherein the anti-brain-tumor drug is administered into a body and then is capable of being guided by an external magnetic field with an intensity in a range from 0.5 tesla (T) to 0.8 (T) to cerebral meninges, and has an antitumor action against cerebral meningioma.

2. The anti-brain-tumor drug according to claim 1, wherein the metal-salen complex compound includes a halide of the metal atom.

3. The anti-brain-tumor drug according to claim 2, wherein the metal-salen complex compound is represented by the following Chemical Formula (I), Chemical Formula (I)

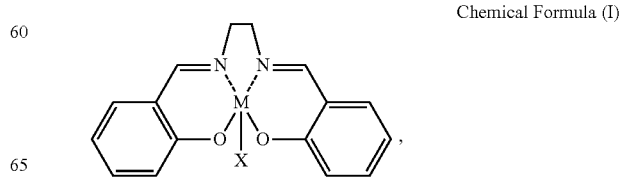

where M is the metal atom, which is Fe, Cr, Mn, Co, Mo, Ru, Rh, W, Re, Os, Ir, Nd, Sm, Eu, or Gd, and X is a halogen atom.

4. The anti-brain-tumor drug according to claim 1, wherein the metal-salen complex compound is an iron-salen complex compound of Chemical Formula (I)

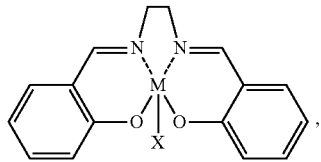

Chemical Formula (I)

and has a crystal structure having the following properties:
  a monoclinic crystal system;
  lattice constants of
    a=14.34(6)Å,
    b=6.907(16)Å,
    c=14.79(4)Å,
    β=96.73(4) degrees, and
    V=1455(8)Å$^3$; and
  a space group of P21/n (#14).

5. The anti-brain-tumor drug according to claim 2, wherein the metal-salen complex compound is an iron-salen complex compound of Chemical Formula (I)

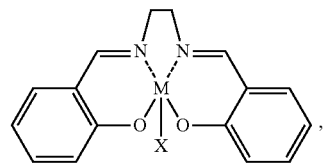

Chemical Formula (I)

and has a crystal structure having the following properties:
  a monoclinic crystal system;
  lattice constants of
    a=14.34(6)Å,
    b=6.907(16)Å,
    c=14.79(4)Å,
    β=96.73(4) degrees, and
    V=1455(8)Å$^3$; and
  a space group of P21/n (#14).

6. The anti-brain-tumor drug according to claim 3, wherein the metal-salen complex compound is an iron-salen complex compound of Chemical Formula (I) and has a crystal structure having the following properties:
  a monoclinic crystal system is monoclinic;
  lattice constants of
    a=14.34(6)Å,
    b=6.907(16)Å,
    c=14.79(4)Å,
    β=96.73(4) degrees, and
    V=1455(8)Å$^3$; and
  a space group of P21/n (#14).

* * * * *